United States Patent [19]

Maggio et al.

[11] Patent Number: 5,837,473
[45] Date of Patent: *Nov. 17, 1998

[54] METHODS OF SCREENING FOR AGENTS AFFECTING THE DEPOSITION OF β-AMYLOID PEPTIDES ON AMYLOID PLAQUES IN HUMAN TISSUE

[75] Inventors: John Edward Maggio, Brookline, Mass.; Patrick William Mantyh, Edina, Minn.

[73] Assignees: President and Fellows of Harvard College, Cambridge, Mass.; Regents of the University of Minnesota, Minneapolis, Minn.

[ * ] Notice: The term of this patent shall not extend beyond the expiration date of Pat. No. 5,434,050.

[21] Appl. No.: 433,734

[22] Filed: May 3, 1995

Related U.S. Application Data

[63] Continuation of Ser. No. 744,767, Aug. 13, 1991, Pat. No. 5,434,050.
[51] Int. Cl.$^6$ .................................................. G01N 33/53
[52] U.S. Cl. ........................... 435/7.21; 435/72; 435/79; 436/518; 436/54; 436/545; 530/324; 530/839
[58] Field of Search ..................................... 435/7.2, 7.21, 435/7.9, 40.5, 40.52; 436/518, 548, 543, 544, 545, 63, 811; 530/387.1, 839, 388.2, 324, 389

[56] References Cited

U.S. PATENT DOCUMENTS

| | | | |
|---|---|---|---|
| 4,666,829 | 5/1987 | Glenner et al. | 435/6 |
| 5,221,607 | 6/1993 | Cordell et al. | 435/7.21 |
| 5,434,050 | 7/1995 | Maggio et al. | 435/7.21 |

FOREIGN PATENT DOCUMENTS

| | | |
|---|---|---|
| 2 223 578 | 4/1990 | United Kingdom . |
| WO 90/05138 | 5/1990 | WIPO . |

OTHER PUBLICATIONS

J.D. Sipe, "Amyloidosis", *Annu. Rev. Biochem.*, 61, 947–975 (1992).
D. Allsop et al., "Immunohistomchemical evidence for the derivation of a peptide ligand from the amyloid β–protein precursor of Alzheimer disease", *Proc. Natl. Acad. Sci. USA*, 85, 2790–2794 (Apr., 1988).
A.E. Bolton et al., "Labelling of Proteins to High Specific Radioactives by Conjugation to a $^{125}$I–Containing Acylating Agent", *Biochem J. 133*, 529–539 (1973).
D. Burdick, et al., "Assembly and Aggregation Properties of Synthetic Alzheimer's A4/β Amyloid Peptide Analogs", *Bio. Chem.*, 267, 546†(1992).
J.E. Castano, et al., "In Vitro Formation of Amyloid Fibrils from Two Synthetic Peptides of Different Lengths Homologous to Alzheimer's Disease β–Protein", *Biochem. Biophys. Res. Commun.*, 141, 782–789 (1986).
C.M. Deber, *Peptides, Structure and Function*, pp. 221–224 and 249–252, Pierce Chemical Company, Rockford, Illinois (1985).
J.F. Flood et al., "Amnestic effects of mice of four synthetic peptides homologous to amyloid β protein from patients with Alheizmers disease", *Proc. Natl. Adad. Sci. USA*, 88, 3363–3366 (Apr. 1991).
M. Goedert et al., "Cloning and sequencing of the cDNA encoding an isoform of microtubule–associated protein tau containing four tandem repeats: differential expression of tau protein mRNAs in human brain", *The EMBO Journal, 8*, 393–399 (1989).
K. Halverson et al. "Molecular Determinants of Amyloid Deposition in Alzheimer's Disease: Conformational Studies of Synthetic β–Protein Fragments", *Biochemistry*, 29, 2639–2644 (1990).
W.S. Hancock, *CRC Handbook of HPLC for the Separation of Amino Acids, Peptides, and Proteins (vol. II)*, pp. 3–22, 279–286 and 303–312, CRC Press, Inc., Boca Raton, Florida (1984).
P.N. Hawkins et al., "Diagnostic imaging of amyloidosis", *European Journal of Nuclear Medicine*, 15(8), 436(Abstract No. 149) (1989).
C. Hilbich et al., "Aggregation and Secondary Structure of Synthetic Amyloid βA4 Peptides of Alzheimer's Disease", *J. Mol. Biol.*, 218, 149–163 (1991).
W.M. Hunter et al., "Preparation of Iodine–131 Labelled Human Growth Hormone of High Specific Activity", *Nature*, 194, 495–496 (May 5, 1962).
C. Joachim, et al., "Amyloid β–protein deposition in tissues other than brain in Alzheimer's disease", *Nature*, 341, 226–230 (Sep. 21, 1989).
J. Kang, et al., "The precursor of Alzheimer's disease amyloid A4 protien resembles a cell–surface receptor", *Nature*, 325, 733–736 (Feb. 19, 1987).
R. Katzman et al., "Advances in Alzheimer's disease", *The FASEB J.*, 5, 278–286 (Mar. 1991).
D.A. Kirshner et al., "Synthetic peptide homologous to β protien from Alzheimer disease forms amyloid–like fibrils in vitro", *Proc. Natl. Acad. Sci. USA*, 84, 6953–6957 (Oct. 1987).
J.–Y. Koh et al., βAmyloid protein increases the vulnerability of cultured cortical neurons to excitotoxic damage, *Brain Res.*, 533, 315–320 (1990).
J.E. Maggio, "Tachykinis", *Ann. Rev. Neurosc.*, 11, 13–28 (1988).
J.Maggio, "Tachykinins and Tachykinin Receptors", Abstract of National Institutes of Health Grant No. NS–22961 (Abstract obtained from Dialog's Federal Research in Progress on–line database).

(List continued on next page.)

Primary Examiner—Marianne P. Allen
Assistant Examiner—Patricia A. Duffy
Attorney, Agent, or Firm—Mueting, Raasch, Gebhardt & Schwappach, P.A.

[57] ABSTRACT

The present invention provides a labelled β-amyloid peptide or a labelled active fragment of β-amyloid peptide and methods of using the labelled peptides to screen for agents which affect the deposition of the labelled peptide onto amyloid plaques in tissue samples evidencing the presence of Alzheimer's amyloidosis.

7 Claims, 8 Drawing Sheets

OTHER PUBLICATIONS

P.W. Mantyh et al., "Substance P receptor binding sites are expressed by glia in vivo after neuronal injury", *Proc. Natl. Acad. Sci. USA*, 86, 5193–5197 (Jul. 1989).

P.W. Mantyh et al., "Peripheral Nociceptors in Inflammation", Abstract of National Institutes of Health Grant No. NS–23970 (Abstract obtained from Dialog's Federal Research in Progress on–line database).

G.R. Marshall, *Peptides, Chemistry and Biology*, pp. 198–201 (Beilan et al.), ESCOM Science Publisers, Netherlands (1988).

S.S. Mirra et al., "The Consortium to Establish a Registry for Alzheimer's Disease (CERAD). Part II. Standardization of the neuropathologic assessment of Alzheimer's disease", *Neurology*, 41, 479–486 (Apr. 1991).

J.C Morris et al., "The Consortium to Establish a Registry for Alzheimer's Disease (CERAD). Part I. Clinical and neuropsychological assessment of Alzheimer's disease", *Neurology*, 39, 1159–1165 (Sep., 1989).

B. Muller–Hill et al., "Molecular Biology of Alzheimer's Disease", *Ann. Rev. Biochem.*, 58, 287–307 (1989).

R.J. Perry, "Recent Advances in Neuropathology", *Br. Med. Bull.*, 42, 34–41 (1986).

P.E. Petrides and J.E. Shively, "Microisolation of Biologically Active Polypeptides by Reverse–Phase Liquid Chromatography" and Reverse–Phase HPLC Isolation and Microsequence Analysis in *Methods of Protein Microcharacterization, A Practical Handbook;* pp. 3–87; Human Press: Clifton, New Jersey (1986).

Remington's, (18th Ed.); "Medical Applications of Radio-isotopes," *Pharmaceuticals Science,* 33, 634–635, 748–749, Ed. A. R. Gennero (1990).

N.K. Robakis et al., "Molecular cloning and characterization of a cDNA encoding the cerebrovascular and the neuride plaque amyloid peptides", *Proc. Natl. Acad. Sci. USA,* 84, 4190–4194 (Jun., 1987).

P. Rovero etal., "Solid–phase synthesis of neurokinin A antagonists", *Int. J. Peptide Protein Res.,* 37, 140–144 (1991).

D.H. Schlesinger, *Macromolecular Sequencing and Synthesis, Selected Methods and Applications,* pp. 153–220, Alan R. Liss, Inc., New York (1988).

D.J. Selkoe, "The Molecular Pathology of Alzheimer's Disease", *Neuron,* 6, 487–498 (Apr.1991).

D.J. Selkoe, "Deciphering Alzheimer's Disease: The Amyloid Precursor Protein Yields New Clues", *Science,* 248, 1058–1060 (Jun. 1990).

D.J. Selkoe, "Biochemistry of Altered Brain Proteins in Alzheimer's Disease", *Ann. Rev. Neurosci.,* 12, 463–490 (1989).

J.M. Stewart et al., Solid–Phase Peptide Synthesis (2nd edition), pp. 74–103 and 147–168, Pierce Chemical Company, Rockford, Illinois (1984).

H.P. Too et al., "Radioimmunoassay of Tachykinins", *Meth. Neurosci.,* 6, 232–241 (1991).

H.P. Too and M.R. Hanley, "Solubilization and characterization of substance P–binding sites from chick brain membranes", *Biochems. J.,* 252, 545–551 (1988).

J.S. Whitsin et al., "Amyloid β Protein Enhances the Survival of Hippocampal Neurons in Vitro", *Science,* 243, 1488–1490 (Mar. 1989).

C. Wong et al., "Neuritic plaques and cerebrovascular amyloid in Alzheimer disease are antigenically related", *Proc. Natl. Acad. Sci. USA,* 82, 8729–8732 (Dec. 1985).

B.A. Yanker et al., "Neurotrophic and Neurotoxic Effects of Amyloid Effects of β Protein: Reversal by Tachykinin Neuropeptides", *Science,* 250, 279–282 (Oct. 1990).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
            20                  25                  30
Gly Leu Met Val Gly Gly Val Val
            35                  40
```

( 2 ) INFORMATION FOR SEQ ID NO:2:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
            20                  25                  30
Gly Leu Met Val Gly Gly Val Val Ile Ala
            35                  40
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly Ser Asn Lys Gly Ala Ile Ile Gly Leu Met
 1               5                  10
```

METHODS OF SCREENING FOR AGENTS AFFECTING THE DEPOSITION OF β-AMYLOID PEPTIDES ON AMYLOID PLAQUES IN HUMAN TISSUE

This is a continuation of application Ser. No. 07/744,767, filed Aug. 13, 1991 now U.S. Pat. No. 5,434,050.

STATEMENT REGARDING FEDERALLY-FUNDED AND SPONSORED RESEARCH

This invention was made with government support from the National Institutes of Health, NIH grant NS-23970, NS-22961, and NS-26312. The government may have certain rights in this invention.

BACKGROUND OF THE INVENTION

Alzheimer's disease is a widespread progressive dementia affecting a significant fraction of the elderly population. While there have been significant advances in the research over about the last five years, the primary pathology of the disorder remains unknown. The behavioral symptoms of Alzheimer's disease are well known, and include loss of memory and cognitive function. The salient pathological symptom of Alzheimer's disease at autopsy is the presence in certain brain areas of extracellular proteinaceous deposits or plaques called amyloid on the basis of their staining with various reagents.

The extracellular amyloid is deposited both at neuronal and vascular sites, and the density of these deposits in the cerebral cortex and blood vessels correlates positively with the degree of dementia (D. J. Selkoe, *Neuron* 6:487 (1991); D. J. Selkoe, *Science* 248:1058 (1990); B. Muller-Hill et al., *Ann. Rev. Biochem.* 58:287 (1989); R. Katzman et al., *FASEB J.* 5: 278 (1991)). The principal component of both neuritic and vascular plaques in Alzheimer's disease is beta-amyloid peptide (β-amyloid or A4 peptide), a hydrophobic peptide of 39–43 amino acids which is encoded by a gene for a much larger protein termed the amyloid precursor protein (APP). Mature amyloid plaques have a halo of degenerating neurons around a core of the β-amyloid peptide (R. J. Perry, *Br. Med. Bull.* 42:34–41 (1986). To date, neither the processing of APP to β-amyloid peptide nor the genesis of the amyloid deposits has been well understood. The characteristics of β-amyloid peptide deposition and the factors that affect it remain key questions in the pathology of Alzheimer's disease.

At the present time, there is no established test other than brain biopsy for diagnosing Alzheimer's disease antemortem. Further, there is no system to quantify neuropathological changes associated with Alzheimer's disease. In addition, there is no method that has been developed to screen and evaluate agents that may have unique anti-Alzheimer's disease action. There is also no method for in vitro evaluation of anti-Alzheimer's disease agents that does not require a sample of patient tissue.

In view of the present lack of knowledge about the development and progression of Alzheimer's disease, there is a need for agents and methods suitable for the diagnosis and detection of Alzheimer's disease. More particularly, there is a need for compounds and assay techniques that can be employed to screen for potential agents that inhibit or enhance the development of amyloid plaques. Such compounds and methods would be useful in assessing senile plaque formation associated with the onset and progression of Alzheimer's disease.

SUMMARY OF THE INVENTION

These and other objects are achieved by the present invention which is directed to a composition and method that is useful for studying, detecting and monitoring the progression of Alzheimer's disease in a patient. More specifically, the composition and method of the present invention are useful for detecting and quantitating amyloid deposition in vivo and in vitro. Further, the present invention provides methods for screening and testing agents which inhibit or enhance amyloid deposition in human tissue.

The present invention provides a labelled β-amyloid peptide useful for detecting Alzheimer's disease and studying Alzheimer's disease-related conditions. A method for obtaining the labelled β-amyloid peptide is also provided. The method employs essentially dry β-amyloid peptide and rapid formation of a labelled β-amyloid peptide. Preferably, the peptide has the amino acid sequence: H-DAEFRHDSGYEVHHQKLVFFAEDVGSNKGAIIGL'-MVGGVV-OH [SEQ. ID NO:1] or an active fragment of such amyloid peptide. In the preferred embodiment, the β-amyloid peptide is bound to a radioactive label such as radioactive iodine. However, other appropriate labelling agents and techniques, for example, enzymatic or fluorescent labelling of the β-amyloid peptide or active peptide fragment, can be used, either alone or in combination. The labelled peptide can be combined with a pharmaceutically acceptable carrier for in vivo diagnostic and possible therapeutic use.

The present invention relates to various uses of the labelled β-amyloid peptide. One such use is in vitro detection and monitoring of Alzheimer's disease in a patient. This is accomplished by combining a sample of patient tissue with an amount of labelled β-amyloid peptide or active fragment thereof for a period of time effective to allow binding of the labelled peptide or peptide fragment to the tissue. The bound labelled peptide/tissue complex is then detected and, if desired, quantified. In vitro detection and monitoring can be accomplished by numerous techniques, including autoradiographic or homogenate binding assays. Homogenate binding assays can be used to screen for potential therapeutic agents, in particular, the ability of these agents to affect deposition of β-amyloid peptide onto tissue and existing plaques. This includes agents that inhibit or enhance deposition or are capable of breaking up existing plaques. Further, progression of Alzheimer's disease may be monitored by assaying a later-acquired sample of tissue from a patient earlier tested in the same manner as the earlier-acquired sample. The amount of bound peptide or peptide fragment in the two tissue samples is compared to provide an assessment as to the development of the disease in a patient.

According to the present invention, in vivo detection of Alzheimer's disease in a patient is also possible by administering the labelled β-amyloid peptide or active fragment to the patient and detecting the presence of the labelled peptide or peptide fragment bound to the tissue in the patient by known imaging techniques such as positron emission tomography (PET) imaging.

Another aspect of the invention is an in vitro method for screening agents capable of affecting the aggregation of β-amyloid peptide. The method can be used to evaluate agents that inhibit or enhance aggregation. This includes an agent's ability to break up and, in certain cases, to inhibit formation or growth of plaques. Agents screened may be of potential use as therapeutic compositions for treatment of Alzheimer's disease. Screening of agents effecting β-amyloid peptide aggregation can be conducted in a test tube without plaque material. Thus, the present invention provides a technique for assessing agents that affect β-amyloid peptide aggregation that requires no patient tissue sample. In vitro screening of potentially useful Alzheimer's disease agents is accomplished by combining β-amyloid peptide or an active peptide fragment thereof with the potential aggregation affecting agent to be screened in a solution. The amount of β-amyloid peptide aggregation is then detected and assessed to determine the effect of the agent on β-amyloid peptide or peptide fragment aggregation. This can be accomplished either in solution, or by filtration, centrifugation and the like. The aggregation affecting agent to be screened may be combined with the β-amyloid peptide or fragment thereof, either before, at or after the start of the peptide aggregation reaction. Alternatively, the β-amyloid peptide aggregation utilizes an aggregation enhancing agent (e.g., detergent, divalent metal cation) prior to inclusion of the aggregation affecting agent to be screened.

The labelled β-amyloid peptide of the present invention and methods of use described herein provide qualitative and quantitative diagnostic tools for studying and potentially treating Alzheimer's disease. Use of β-amyloid peptide aggregation as a screening tool for compositions having potential therapeutic use provides a previously unavailable technique to study and evaluate potential therapeutic agents without patient tissue.

Other features and advantages of the invention will be apparent from the following detailed description and appended claims.

DETAILED DESCRIPTION OF THE INVENTION

Figure 1:
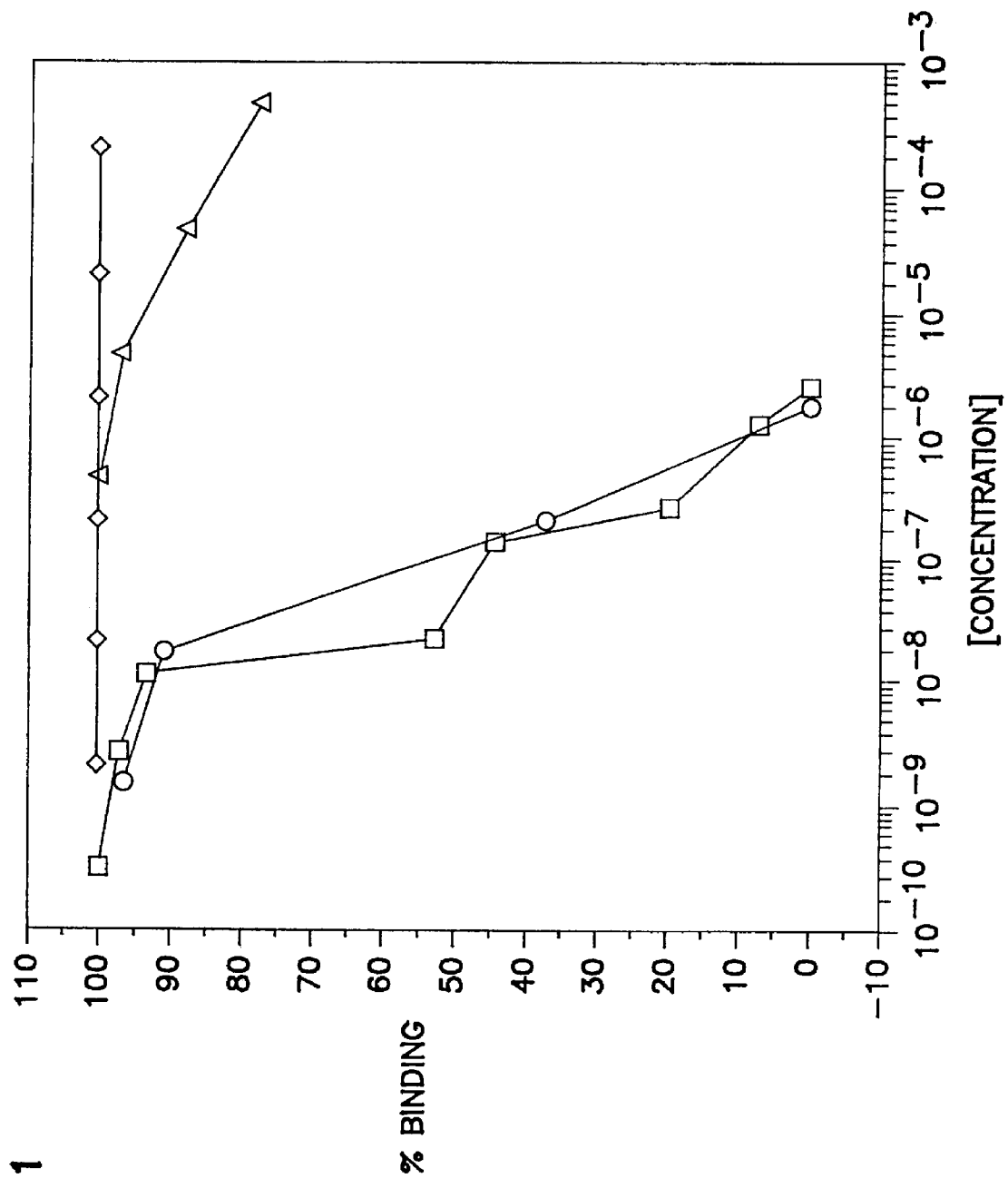
FIG. 1 is a graphic representation of competitive inhibition of specific binding of $^{125}$I-β-amyloid peptide$^{1-40}$ by amyloid and tachykinin peptides in homogenates of Alzheimer's disease temporal cortex. LEGEND: □ β-amyloid peptide$^{1-40}$ (β-AP$^{1-40}$); ● Dutch β-amyloid peptide$^{1-40}$; ■ β-amyloid peptide$^{25-35}$-NH$_2$; and ○ Substance P, Neurokinin A, Neurokinin B, β-amyloid peptide$^{25-35}$-OH, Rat β-amyloid peptide$^{1-40}$.

The present invention provides: a labelled β-amyloid peptide or active (i.e., biologically, or chemically active, or shown as positive in an assay) fragment; a composition including the labelled β-amyloid peptide or active fragment thereof and a pharmaceutical carrier; a method for labelling the β-amyloid peptide or an active fragment thereof, and methods of using the labelled peptide or peptide fragment for detecting or monitoring Alzheimer's disease in a patient.

As used herein, the term "aggregation" refers to the tendency of a large molecule or colloidal body to associate together into a mass or body of units or parts.

Labelled β-amyloid peptide or active fragments are used in the methods according to the invention. β-amyloid peptide has a sequence of about 40 amino acids. The exact length of the naturally-occurring peptide may vary from about 39 to 43 amino acids, depending on the presence of ragged ends. The sequence of the 42-mer peptide is H-DAEFRHDSGYEVHHQKLVFFAEDVGSNKGAIIG-LMVGGVVIA-OH [SEQ. ID NO:2], and the sequence of the 40-mer peptide is H-DAEFRHDSGYEVHHQKLVFFAEDVGSNKGAIIG-LMVGGVV-OH [SEQ. ID NO:1]. The 40-mer peptide is preferred in the present invention. However, active fragments having as few as about 5 amino acids and ranging from about 5 to about 43 amino acid units are useful if appropriate labelling and measuring techniques are used to detect a smaller fragment of the 39- to 43-mer peptide. In particular, a peptide fragment derived from the 1–43 amino acid region of β-amyloid peptide and having at least 10 amino acid units, as for example, a fragment containing the amino acids at about position 25–35, may be used according to the invention.

As used herein, abbreviations for the amino acids are as listed in Table 1, as shown below. In addition, abbreviations for peptide termini are as follows: "H—" means a free amino group, "—OH" means a free carboxyl group, and "—NH$_2$" means a carboxyamide. Sequences are numbered from the amino termini with positions indicated by superscripts.

TABLE I

Amino Acid Codes

| Single letter Code | 3-letter Code | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The β-amyloid peptide or active fragment is combined with an acceptable label as described herein. The label can be radioactive, enzymatic, or fluorescent, or any combination thereof. Preferably, a radioactive label such as radioactive iodine-125 is used.

Among isotopes, any radioactive substance that may be incorporated into the peptide or peptide fragment may be used. Preferred isotopes include, but are not limited to, $^{125}$iodine, and $^{131}$iodine; the latter has a shorter half-life and higher energy level. Iodine radioisotopes may be incorporated into the peptide or peptide fragment by oxidative iodination. Also, radioactive iodine may be incorporated by use of Bolton-Hunter reagent to add a 3-iodo-4-hydroxyphenylpropionyl or 3,5-diiodo-4-hydroxypropionyl group to a nucleophile in the peptide.

Other isotopes may also be incorporated by reaction with nucleophile groups on peptides. For example, tritium ($^3$H) can be incorporated by reaction with propionyl-N-hydroxysuccinimide, or radioactive sulfur ($^{35}$S) can be incorporated by similar reagents. Radioactive phosphorus ($^{32}$P) may be incorporated by enzymatic methods. Additionally, various radioactive metal ions, such as $^{99m}$technetium, may be incorporated into β-amyloid peptide or fragments thereof if an appropriate chelating group is added first.

For detection in in vitro assays according to the present invention, enzyme labelling is also useful. Among the preferred enzyme labels are peroxidases such as horseradish peroxidase (HRP), or phosphatases such as alkaline phosphatase.

Modifying the peptide or peptide fragment by adding an antigenic group that will bind with an antibody allows indirect detection of the peptide or peptide fragment itself. For example, the antigen digoxigenin can be linked to an oligonucleotide or peptide, and then visualized with a labelled digoxigenin-specific antibody, or labelled antiantibody.

Although less sensitive than radioisotopes, fluorophores may also be incorporated into the peptide and detected according to known fluorescent detection techniques. Examples of suitable fluorophores include fluorescein, rhodamine, Texas Red, and the like.

Direct or indirect chemiluminescent labels may also be used according to the invention, such as dioxetanes. For example, the peptide would be modified with a group that is capable of emitting light as it decomposes.

In addition, an avidin-biotin system may be used to detect the peptide or peptide fragment in an in vitro assay. For example, the peptide or fragment may be functionalized with biotin, and avidin or streptavidin added to detect the protein or fragment.

In vitro methods of detecting Alzheimer's disease according to the present invention combine an amount of sample of tissue obtained from a patient with an amount of labelled β-amyloid peptide or active fragment thereof. The tissue sample may be obtained from any tissue in which the growth of amyloid plaques may occur, including, for example, the nasal epithelium, skin and tissue obtained from portions of the brain such as the cerebral cortex, hippocampus and amygdala, and the like. Preferably the tissue sample used is about 1–20 ug/assay tube for tissue prepared in thin section which is preferably about 5–15 μm thick, and about 5–50 mg/assay tube for tissue prepared as a homogenate.

Submicrogram amounts of the labelled β-amyloid peptide or active fragment thereof, for example, about 0.1 to 10 ng of $^{125}$I radiolabelled β-amyloid peptide or fragment thereof, is added to each tissue sample for a time effective for the labelled peptide or peptide fragment to bind with the tissue sample. Preferably, the binding reaction time is about 1 to 5 hours, more preferably about 2 hours under the experimental conditions described herein. The time will vary depending on the specific experimental conditions, as will be understood by one skilled in the art. After reaction of the tissue sample with the labelled peptide or fragment, the tissue sample is preferably washed with an appropriate buffer to remove unbound labelled peptide. Homogenized tissue samples are preferably filtered prior to the washing step.

The assay preferably includes a negative control, for example, normal tissue in which binding of β-amyloid peptide is substantially negligible or about 10000 CPM (5% of the total isotope) under the experimental conditions described herein for homogenate binding assays, or less than about 25% of that exhibited in individuals with clinically diagnosed Alzheimer's disease (see Table II, below). The assay may further include a positive control of, for example, tissue that is positive for Alzheimer's disease.

Table II. Summary of clinicopathological features of control and Alzheimer's disease patients compared with the concentration of plaques detected with the $^{125}$I-β-amyloid peptide 40 technique.

For tissue with identification numbers (ID#) ending with "-D", the CERAD clinical, neuropsychological and neuropathological was used to confirm the diagnosis of Alzheimer's disease (J. C. Morris et al., *Neurology* 39: 1159 (1989); S. S. Mirra et al, *Neurology* 41: 479 (1991), the disclosures of which are incorporated by reference herein. The diagnosis of Alzheimer's disease for tissue with identification numbers (ID#) ending with "-R", was based on clinical assessment by the primary physician and neuropathological examination.

| ID # | Age/Sex | PM Interval[1] | Diagnosis[2] | Region[3] | P[4,6] | BV[5,6] |
|---|---|---|---|---|---|---|
| H 001-D | 76 yrs/F | 49 Minutes | AD | T | ++++ | ++ |
| H 002-D | 84 yrs/F | 48 Minutes | AD | F | ++++ | + |
| H 003-D | 79 yrs/M | 53 Minutes | AD | T | ++++ | ++++ |
| H 004-D | 67 yrs/F | 25 Minutes | AD | F, T | ++++ | – |
| H 005-D | 78 yrs/F | 46 Minutes | AD | T | ++++ | ++ |
| H 006-D | 79 yrs/M | 63 Minutes | AD | T | ++++ | + |
| H 017-R | 73 yrs/F | 13 Hrs. 22 Min. | AD | T | ++ | |
| H 020-R | 63 yrs/M | 5 Hrs. 22 Min. | AD | T | ++++ | + |
| H 023-R | 70 yrs/F | 5 Hrs. 30 Min. | AD | T | | |
| H 007-D | 59 yrs/F | 100 Minutes | Control | F, T | – | – |
| H 008-D | 63 yrs/F | 103 Minutes | Control | T | – | – |
| H 009-D | 59 yrs/F | 80 Minutes | Control | T | – | – |
| H 010-D | 70 yrs/M | 135 Minutes | Control | T | – | – |
| H 019-R | 75 yrs/F | 10 Hrs. 33 Min. | Control | T | – | – |
| H 022-R | 63 yrs/M | 5 Hours | Control | T | + | – |
| H 018-R | 75 yrs/M | 13 Hours | Parkinson's | T | +++ | – |
| H 021-R | 60 yrs/M | 11 Hrs. 20 Min. | Parkinson's | F | – | – |

[1]PM = post-mortem
[2]AD = Alzheimer's disease.
[3]T = temporal cortex; F = frontal cortex.
[4]P = parenchyma of cerebral cortex.
[5]BV = blood vessel in cerebral cortex.
[6]concentration of plaques observed in P or BV: (–), not detectable; (+), light; (++), moderate; (+++), dense; (++++), very dense.

The in vitro detecting and monitoring techniques according to the present invention can be qualitative or quantitative. The presence of tissue-bound labelled peptide or peptide fragment may be detected according to known techniques appropriate for the particular labelling agent and method used (e.g., radioisotope, fluorophore, enzyme, antigen), the tissue sample type (e.g., homogenate, thin slice), the particular peptide or fragment used (e.g., β-amyloid peptide$^{1-40}$, β-amyloid peptide$^{25-35}$), and other factors of the assay. In addition, the method of detecting radioactive isotopes will vary according to the isotope and its corresponding energy level. For example, a gamma counter is capable of detecting $^{125}$iodine, but not tritium ($^3$H) or $^{35}$sulfur.

Where radiolabelling is used to label the peptide or fragment, the peptide/tissue complex may be detected by various known radioisotope detection techniques. For example, positron emission tomography may be used to detect isotopes that emit positrons such as radioactive $^{18}$fluorine or $^{11}$carbon, gamma counters to detect radioactive $^{125}$iodine, and scintillation counting methods in the case of tritium ($^3$H). Nuclear magnetic resonance imaging may also be used, in which case the label would contain a magnetically active particle.

Autoradiography is preferably used to visualize radiolabelled peptides or peptide fragments in tissue sections, and a radiation counter such as a gamma counter or scintillation counter preferred to detect radioisotopes in tissue samples prepared as a homogenate.

In vivo detection and monitoring of Alzheimer's disease includes administering the labelled β-amyloid peptide or active fragment thereof to a patient in an amount effective to bind with tissue evidencing the presence of, or susceptible to, Alzheimer's disease. Like in vitro detecting methods, the presence of the labelled peptide or peptide fragment bound to tissue in the patient is detected by a known detecting technique that is appropriate to the tissue sample type, the particular peptide or fragment used, the labelling method used, and other such factors unique to the particular assay being performed.

For medical imaging, the label should be detectable outside of the body. Preferably, the label is a positron emitting radioisotope with a relatively short half-life, such as $^{11}$carbon or $^{18}$fluorine. Such an isotope may be imaged by positron emission tomography, or PET scanning. Magnetic resonance imaging may also be used, in which case the label would include a magnetically active particle.

The present invention also provides useful methods to detect, monitor and screen potential therapeutic agents for affecting Alzheimer's disease. In particular, methods for in vitro screening of agents that are capable of inhibiting or enhancing the aggregation of β-amyloid peptide or active fragments thereof, including the ability to break up and, in certain cases, to inhibit formation or growth of plaques, are provided. According to one method, potential therapeutic agents are placed in competition with labelled β-amyloid peptide in a solution with sample patient tissue, and the effect of the test agent on β-amyloid peptide binding to same tissue is quantified.

Another method is based on the finding that β-amyloid peptide will self-aggregate (i.e., aggregation of β-amyloid molecules based solely on concentration) in solution. This method is particularly advantageous since no patient tissue is required. The aggregation of β-amyloid peptide is dependent primarily on the concentration of the peptide or peptide fragment. For example, an about $10^{-4}$ molar aqueous buffer solution of β-amyloid peptide$^{1-40}$ will commence self-aggregation within a period of about 5 to 30 minutes. At lower concentrations, β-amyloid peptide aggregation may take from about 1 to 5 hours or longer.

In a β-amyloid peptide aggregation screening test, β-amyloid peptide or a peptide fragment thereof is combined with an acceptable buffer or solvent and an agent to be tested. After a specified period, for example 1 to 2 hours, the amount of aggregation is determined. The amount of aggregation can also be periodically monitored over a set time period. More specifically, after a period of time effective to allow aggregation of the peptide or peptide fragment in the solution, for example about 5 to 60, or preferably about 15 to 30 minutes, a potential aggregation affecting agent is added. Alternately, the aggregation affecting agent to be screened may be added at or before the start of aggregation of the peptide. The inhibiting or enhancing effect of the agent is subsequently determined.

To enhance aggregation of the peptide or fragment, an aggregation enhancing or promoting agent may be combined with the peptide or peptide fragment prior to addition of the aggregation affecting agent. For example, the enhancing agent may be a small amount of pre-formed aggregate of the peptide or peptide fragment, a small amount of purified amyloid plaque derived from Alzheimer's disease tissue, or a substance capable of expediting the aggregation, as for example, about 0.01 to 2% of a detergent such as digitonin, sodium dodecylsulfate (SDS), 3-[(3-cholamidopropyl) dimethylammonio]-1-propanesulfanate) such as CHAPS available from Sigma Chemical Company (St. Louis, Mo.), or octoxynol such as Triton X-100 available from Sigma Chemical Company (St. Louis, Mo.). With resect to deposition of the labelled peptide on tissue plaques, an amount of about 0.1 to 50 millimolar of a metal ion such as manganese ($Mn^{+2}$) or zinc ($Zn^{+2}$) can act as an enhancing agent. The aggregation enhancing agent is added to the peptide/fragment solution in an amount effective to initiate or promote aggregation of the peptide or peptide fragment.

In yet another embodiment, the invention provides a pharmaceutical composition for in vivo use in detecting Alzheimer's disease in a human tissue. The composition contains labelled β-amyloid peptide or active peptide fragment thereof, in a pharmaceutically-acceptable carrier of the type appreciated by those of skill in the art. The composition contains the labelled peptide or peptide fragment in an amount effective to bind to tissue evidencing the presence of, or susceptible to, Alzheimer's disease, when administered in vivo.

The labelled β-amyloid peptide or peptide fragment is useful to detect or quantify the presence of, or tissue susceptibility to, Alzheimer's disease in human tissue. With respect to an in vitro tissue binding assay, the amount of labelled peptide or fragment is effective to bind with tissue evidencing the presence of, or susceptibility to, Alzheimer's disease. Such a binding assay can be used to test agents that may be useful anti-Alzheimer's disease compositions.

The aggregation assay described herein provides a technique to screen potential therapeutic agents. In an aggregation assay, the A-amyloid composition will contain the peptide or fragment in an amount effective to self-aggregate, or an amount of β-amyloid peptide together with the chosen aggregation enhancing agent.

EXAMPLE 1

Preparation of Labelled β-Amyloid Peptide

A radiolabelled amyloid peptide, $^{125}$I-labeled β-amyloid peptide$^{1-40}$, was synthesized for use in determining binding properties of human β-amyloid peptide tissues in homogenates, and to characterize binding to localize tissue sites with which the peptide interacts in thin sections of normal or Alzheimer's disease tissue including central nervous system and vascular tissue.

Preparation of peptide.

Unlabelled peptides of human β-amyloid peptide$^{1-40}$—OH and β-amyloid peptide$^{25-35}$—OH can be purchased from Bachem, Torrance, Calif. Alternatively, the peptide can be synthesized by solid-phase fluorenylmethoxycarbonyl ("Fmoc") chemistry using techniques described, for example, in J. M. Stewart and J. D. Young, Solid-Phase Peptide Synthesis (2nd edition), pages 74–103 and 147–168, Pierce Chemical Company, Rockford, Ill. (1984); C. M. Deber, *Peptides, Structure and Function*, pages 221–224 and 249–252, Pierce Chemical Company, Rockford, Ill. (1985); D. H. Schlesinger, *Macromolecular Sequencing and Synthesis, Selected Methods and Applications*, pages 153–220, Alan R. Liss, Inc., New York (1988); and G. R. Marshall, *Peptides, Chemistry and Biology*, pages 198–201, ESCOM Science Publishers, Netherlands (1988), the disclosures of which are incorporated by reference herein. It has been shown that the Fmoc strategy offers considerable advantages over the traditional Boc method for preparation of hydrophobic peptides (P. Rovero et al., *Int. J. Peptide Protein Res.* 37:140 (1991)). The resin used was polystyrene crosslinked with divinylbenzene and functionalized with an acid-labile linker. Sidechains were blocked with standard acid-labile blocking groups such as BOC, TMOB, and PMC. Alpha-amino groups were blocked with Fmoc. All activations were by diisopropylcarbodiimide and hydroxybenzotriazole in dichloromethane, except Gln and Asn, which were introduced as active (pentafluorophenyl) esters without further activation in dimethylformamide ("DMF") solution. Two hour couplings were used at each stage of the synthesis. A fourfold molar excess of amino acid monomer over peptide resin was used at each step. Removal of the Fmoc group after each coupling was achieved with 30% piperidine in 1:1 DMF:toluene for 5 and 15 minutes consecutively. Extensive washings of the resin between chemical steps was with both DMF and DMF:dichloromethane 1:1. Following the final coupling and deblocking cycle, the peptide resin was washed extensively with DMF, DMF:dichloromethane 1:1, and methanol. The peptides were cleaved from the resin using anhydrous trifluoroacetic acid containing 5% thianisole, 3% ethanedithiol, and 2% anisole as scavengers.

The peptides were purified to homogeneity by reverse-phase HPLC using a $C_{18}$-column eluted with a gradient of acetonitrile in 0.01M aqueous TFA according to standard methods, such as those described in J. E. Shively, *Methods of Protein Microcharacterization, A Practical Handbook*, pages 3–88, Humana Press, Clifton, N.J. (1986), and W. S. Hancock, *CRC Handbook of HPLC for the Separation of Amino Acids, Peptides, and Proteins* (Vol. II), pages 3–22, 279–286 and 303–312, CRC Press, Inc., Boca Raton, Fla. (1987), the disclosures of which are incorporated by reference herein.

All peptides were further characterized by amino acid analysis and/or peptide sequencing according to standard methods such as those described in Shively supra. Peptides were stored at −20° C. as dry lyophilizates or as stock solutions of $10^{-3}$M concentration in the solvents in which they were purified, i.e., in the HPLC solvents in which they eluted from the $C_{18}$ HPLC column, with 1% 2-mercaptoethanol added as antioxidant. The composition of these solvents varied from 25% to 35% acetonitrile in aqueous 0.01M TFA, with no evidence of peptide oxidation, aggregation, or degradation apparent over 4 months. In contrast, storage of the peptides in common solvents used for peptide stock solutions such as water, dimethylsulfoxide, glacial acetic acid, or dimethylformamide gave significant oxidation, aggregation, or degradation resulting in materials not suitable for use in the procedures described below.

Except as otherwise noted, all peptides were based on the human β-amyloid peptide sequence. Accordingly, β-amyloid peptide$^{1-42}$ is H-DAEFRHDSGYEVHHQKLVFFAEDVGSNKGAIIGL-MVGGVVIA-OH [SEQ. ID NO:2]. The analogous peptide in rat and mouse ($G^5$, $F^{10}$, $R^{14}$-β-amyloid peptide$^{1-42}$) differs at three positions within that sequence. Dutch β-amyloid peptide ($Q^{22}$-β-amyloid peptide$^{1-42}$) differs at one position within this sequence. The sequence of β-amyloid peptide$^{25-35}$-NH$_2$ is H-GSNKGAIIGLM-NH$_2$ [SEQ. ID. NO.:3].

Procedure for radioiodination of β-amyloid peptide$^{1-40}$.

Peptides containing tyrosine were radiolabelled by oxidative radioiodination using Na$^{125}$I and chloramine-T and separated from free iodide by reverse-phase absorption by modifications described hereinbelow of the methods of W. M. Hunter and F. C. Greenwood, *Nature* 194:495 (1962), A. E. Bolton and W. M. Hunter, *Biochem. J.* 133:529 (1973), and H. -P. Too and J. E. Maggio, *Meth. Neurosci.* 6:232 (1991), the disclosures of which are incorporated by reference herein. Peptides not containing tyrosine were first acylated with the N-hydroxysuccinimide ester of 4-hydroxyphenylpropionic acid, and then oxidatively radioiodinated as indicated hereinbelow. Briefly, labelled peptides containing methionine were then reduced from sulfoxide to native form with 2-mercaptoethanol. The iodinated peptides were purified by RP-HPLC to essentially quantitative specific activity (approximately 2000 Ci/mmol) and stored as described hereinabove at a concentration of less than 200,000 dpm/µl.

Acylation with the N-hydroxysuccinimide ester of 4-hydroxyphenylpropionic acid followed the method of H. -P. Too and J. E. Maggio, *Meth. Neurosci.* 6: 232 (1991), the disclosure of which is incorporated by reference herein. Care was taken to purify for future labelling only the monoacyl derivatives of the peptides, which were recognized by their elution profiles.

Standard radioiodination procedures such as those described in W. M. Hunter and F. C. Greenwood, supra, A. E. Bolton and W. M. Hunter, supra, and H. -P. Too and J. E. Maggio, supra, do not yield a viable tracer. It was found that iodination of the peptide must be performed at high buffer salt concentration (0.5M sodium phosphate, pH 7.5). However, since under those conditions solutions of the peptide are substantially unstable, it is necessary to perform the iodination step quickly. Preferably the labelling reaction from the point of dissolving the peptide in the phosphate buffer to loading the reaction mixture onto an octyldecyl-silica cartridge is completed within about one minute. If this part of the procedure is not completed in a sufficiently short period of time, the β-amyloid peptide will aggregate and fail to yield useful tracer.

It was found that successful iodination of the β-amyloid peptide requires starting with the peptide in its dry form. It was found that peptide placed in typical solvents such as aqueous buffer or dimethylsulfoxide did not yield a viable tracer. It was further found that the peptide remains stable in the solvent in which it is purified (35% acetonitrile in 0.01M aqueous TFA). Thus, the peptide (10 nmol) is loaded into the reaction vessel (a polypropylene microcentrifuge tube) by placing an aliquot of peptide solution in this solvent in the reaction vessel and then stripping the solvent in a vacuum centrifuge. It is preferred that a high molar ratio of peptide to radioiodine is used to minimize diiodination since the monoiodinated form is preferred for use in the assays described herein.

It was found that the labelled peptide is viable as a tracer only when in the reduced (native methionine sidechain) form at high specific activity. Therefore additional steps of reduction and purification to high specific activity are necessary after the labelling reaction and its workup. Typical radioiodination syntheses are halted after labelling and the products used without additional steps. Such products, consisting of low specific activity peptides containing oxidized methionine, are acceptable for the majority of applications of peptide tracers such as radioimmunoassay. It was found that production of viable β-amyloid peptide tracer requires the additional steps of reduction and purification as described hereinbelow.

It was determined that in order to avoid aggregation of the labeled peptide and consequent loss of viable tracer during the reduction reaction, the reaction time must be 90 minutes or less. Although reduction of the sulfoxide form is not complete at 90 minutes, the labelled β-amyloid peptide remains mostly as intact monomer. Longer reaction times provide more complete reduction at the risk of formation of unusable aggregates.

The purification of the monoiodinated reduced tracer is accomplished by reverse-phase HPLC using a shallow gradient of acetonitrile in aqueous 0.01M TFA which is capable of resolving oxidized from reduced forms, and uniodinated from monoiodinated from diiodinated forms of the β-amyloid peptide. It is preferred that the reduced monoiodinated form of the peptide is used in the assays described below.

To 10 nmol of dry β-amyloid peptide$^{1-40}$ in a polypropylene microcentrifuge tube is added 40 μl of 0.5M sodium phosphate pH 7.5 and 10 μl (=1 mCi) of aqueous Na$^{125}$I, and the tube is vortexed briefly. Chloramine-T (10 μl of 1 mg/ml in distilled water, freshly dissolved) is added to the mixture and the tube vigorously vortexed for 15 to 30 seconds. The reaction is then terminated by the addition of Na$_2$S$_2$O$_5$ (20 μl of 10 mg/ml in distilled water), followed by brief vortexing.

The reaction mixture is immediately loaded onto an octyldecylsilica cartridge (volume approximately 0.5 ml) previously primed by washing with 3 ml acetonitrile containing 0.01M TFA followed by 3 ml 0.01M aqueous TFA. Examples of suitable octyldecylsilica cartridges include C$_{18}$ SPICE (Analtech), C$_{18}$ spe (Baker), and C$_{18}$ Sep-Pak (Waters). The octyldecylsilica cartridge is then eluted in step gradient fashion successively with 0.5 ml each of 0.01M aqueous TFA containing 10%, 20%, and 40% alcohol, and then eluted with 1 ml each of 80% and 100% alcohol, where alcohol is methanol:ethanol in a 1:1 volume. The labelled peptide of interest elutes in the 80% alcohol fraction. During elution of the cartridge, it is preferred that a slow flow rate is used, that air bubbles are avoided, and that the cartridge not be allowed to dry out to avoid adverse affects on the yield of labelled peptide.

The labelled peptide fraction which elutes from the octyldecylsilica cartridge includes the oxides of unlabelled, monoiodinated, and diiodinated peptides in alcoholic aqueous 0.01M TFA. Chemical reduction to the native methionine forms is accomplished by concentrating the solution to less than about 25% of its original volume by gently evaporating the alcohol in a nitrogen stream, then adding neat 2-mercaptoethanol to a final concentration of 20%, and heating the resulting solution in a tightly capped tube under nitrogen at 90° C. for 90 minutes. After cooling to room temperature, the mixture is purified by reverse-phase HPLC as described above, and the appropriate radioactive peptide (the reduced, monoiodinated form) retained for future use. Immediately following purification, 1% 2-mercaptoethanol is added to the purified tracer to prevent oxidation to the useless sulfoxide form. The tracer, now preferably at 2000 Ci/mmol (for $^{125}$I), is stored as indicated above. At −20° C., solutions of less than 200,000 dpm/μl are stable for at least 4 months.

EXAMPLE 2

Detection of In Vivo β-Amyloid Peptide Deposition in Human Tissue and Use of Labelled β-Amyloid Peptide Preparation of tissue homogenates and thin sections.

Brain tissue was obtained from normal and Alzheimer's disease patients at 0.5 to 14 hours postmortem, frozen on dry ice after collection, and stored at −20° C. until use. For filter binding studies, tissue homogenates were prepared after the method of H. P. Too and M. R. Hanley, *Biochem. J.* 252:545 (1988), the disclosure of which is incorporated by reference herein. Tissue was homogenized (Polytron, setting 7–8, 5–10 sec) in 5–10 volumes of 50 mM Tricine (pH 7.5) containing 10% sucrose and protease inhibitors (0.01% bacitracin, 0.002% soybean trypsin inhibitor, 0.0002% chicken egg trypsin inhibitor, 1 mM benzamidine hydrochloride) and pelleted at 10,000 g for 20 minutes. The homogenate was then resuspended and washed several times in Tricine buffer containing 120 mM NaCl, 10 mM EDTA, 300 mM KCl and centrifuged at 40,000 g for 20 minutes and stored at −20° C. for less than two months. Membranes (equivalent to about 30 mg tissue) were resuspended in 0.5 ml 50 mM TrisHCl (pH 7.5) containing 1 mg/ml bovine serum albumin (BSA), 10 mM MnCl$_2$, 0.004% bacitracin, 0.002% chymostatin, 0.004% leupeptin, 0.1% dimethylsulfoxide for 30 minutes prior to addition of the radioligand ($10^{-11}$ to $10^{-9}$M) and various concentrations of unlabelled peptides in the same buffer.

After incubating for two hours at room temperature, the homogenates (final volume 0.575 ml) were filtered through glass fiber filters (Whatman GF/D), presoaked for at least two hours in 1 mg/ml BSA and rinsed with 25 mM Tricine (pH 7.5). After washing twice with 25 mM TrisHCl (pH 7.5) at room temperature, the filters were counted in a gamma counter. Signal/noise and specific binding were a function of the density of plaques in the tissue.

In Alzheimer's disease tissue homogenates, about 20,000 cpm (20%) of the $^{125}$I-labeled β-amyloid peptide$^{1-40}$ was bound in the absence of unlabelled peptides, and 10000 cpm (10%) in the presence of $10^{-5}$M unlabelled β-amyloid peptide$^{1-40}$. No displacement binding was observed when plaques were absent (i.e., in normal tissue). Autoradiography of the homogenate confirmed that the highest density of binding sites in Alzheimer's disease tissue was on intact plaques.

Autoradiography.

For tissue autoradiography, unfixed tissue was serially sectioned at 5–15 μm and thaw-mounted onto gelatin-coated slides. Slide-mounted sections were stored at −20° C. in closed boxes over desiccant for less than three months before use. Sections were preincubated for 30 minutes and incubated with the radioligand for two hours under the same conditions according to the aforedescribed homogenate binding study. Alternatively, 50 mM TrisHCl rather than Tricine may be used as the buffer. For estimating nonspecific binding, paired serial sections were incubated with the radioligand in the presence of a $10^4$ to $10^5$ fold excess of the unlabelled peptide. Following incubation with the radioligand, the slides were washed with 50 mM TrisHCl pH 7.5 (four times, two minutes each at 4° C.), then dried at 4° C. and stored in closed boxes over desiccant at room temperature overnight. The fully dried slides were then placed in apposition to tritium-sensitive film alongside iodinated standards. After one week's exposure at −20° C., the film was developed, fixed and washed. Sections were later dipped in photographic emulsion for higher resolution autoradiography and/or counterstained by standard procedures with Congo red, thioflavin S, creosyl violet, hematoxylin and eosin, or antibodies for immunohistochemical analysis. This approach generated film autoradiograms for quantitative densitometry, a high resolution emulsion autoradiograms for detailed histology, and a counterstained section for identification of cell types from each tissue section.

RESULTS.

While there was essentially no displaceable binding of the radioligand to normal tissue homogenates or sections, there was significant displaceable binding to Alzheimer's disease tissue (see FIGS. 1 and 2). The binding to Alzheimer's disease tissue was not saturable, suggesting that most of the sites to which the radioligand bound were not receptors in the usual sense (i.e., receptor directly coupled to an effector mechanism that directly affects the intra-cellular environment). Rather, the characteristics of this binding were consistent with growth of Alzheimer's disease amyloid plaques by deposition of β-amyloid peptide from solution.

Radiolabelled human β-amyloid peptide was deposited in vitro from dilute ($<10^{-11}$M) solution onto neuritic, diffuse, and cerebrovascular plaques in AD brain tissue, within 30 to 60 minutes. In tissue without preformed plaques, no deposition was detected. These results indicate that all three types of plaques are capable of growth through deposition of exogenous amyloid peptide in the presence of very low amounts of β-amyloid peptide. These results further indicate that plaque growth alone does not explain the selective damage to particular subsets of neurons which typifies the disease process.

Visualization of the binding sites for $^{125}$I-β-amyloid peptide$^{1-40}$ by autoradiography showed that the ligand was deposited on amyloid plaques at both parenchymal and vascular sites in Alzheimer's disease brain. Thus, in the Alzheimer's disease cerebral cortex, $^{125}$I-β-amyloid peptide$^{1-40}$ was deposited on both the core and the halo of essentially every extracellular plaque examined (FIG. 2). In the Alzheimer's disease cerebellar cortex, diffuse plaques which were not visualized with thioflavin S were readily labelled with the β-amyloid peptide radioligand (see FIG. 2), and clear morphological differences between these plaques and the compact plaques of the cerebral cortex were evident. Thus, both the classic senile plaques of the cortex and the diffuse nonneuritic deposits of the cerebellum were found capable of in vitro growth by addition of β-amyloid peptide from dilute solution. While thioflavin S and anti-A4 antibodies stained neurons outside the plaques as well as the plaques themselves, deposition of the radioligand was limited to the plaques alone (see FIG. 2). Furthermore, the sensitivity of detection of plaques with the radioligand far exceeded that of dyes or antibodies. Thus, the radioligand was capable of detecting more lesions at a potentially earlier time than detection techniques reported to date. In cerebral cortex tissue obtained from normal brain, there was essentially no deposition of β-amyloid peptide radioligand detected above background levels at parenchymal or vascular sites.

Vascular plaques were visualized by β-amyloid peptide deposition in approximately 0–20% of intra- and extraparenchymal blood vessels in Alzheimer's disease brain, although the fraction of vessels labelled showed considerable variation between cortical areas examined and between patients (See Table II). The cerebrovascular deposits were consistently labelled more densely than cerebral plaques within the same section. In vessels seen in transverse section (see FIG. 3), the deposition of β-amyloid peptide radioligand was not uniform but concentrated in a part of the vessel, apparently the tunica media. Endothelial tissue was not labeled.

Deposition of $^{125}$I-β-amyloid peptide$^{1-40}$ onto plaques in both homogenates and sections of Alzheimer's disease tissue was significantly attenuated by excess unlabelled β-amyloid peptide$^{1-40}$ and Dutch β-amyloid peptide$^{1-40}$, as addition of these unlabelled peptides to the plaques competed with deposition of the radioligand (see FIG. 1). β-amyloid peptide$^{25-35}$—NH$_2$ also competed with the 40-mer radioligand when the former was present at higher concentrations (see FIG. 1), while the free acid β-amyloid peptide$^{25-35}$—OH had no detectable activity in the assay. Thus, the growth of amyloid plaques in vitro required only the presence of β-amyloid peptide in the surrounding media. The affinity of the amyloid peptide for the plaques was sufficiently high that even when the concentration of β-amyloid peptide1-40 was below $10^{-11}$M, deposition occurred. No significant differences in β-amyloid peptide deposition were noted between homogenates and sections of Alzheimer's tissue nor were any significant differences noted between Alzheimer's disease cerebral cortex (neuritic plaques) and cerebellum (diffuse plaques). These results were consistent with the hypothesis that the plaques themselves (neuritic, diffuse, and vascular) can grow in vivo in the presence of β-amyloid peptide.

The mammalian tachykinins, substance P and neurokinins A and B, over a broad range of concentration, did not inhibit the deposition of radiolabelled β-amyloid peptide onto Alzheimer's disease plaques (see FIG. 1). Binding sites for radiolabelled tachykinins were present in both Alzheimer's disease and normal tissue, and were not associated with plaques. These tachykinin binding sites were indistinguishable from the tachykinin receptors that have been described by J. E. Maggio, *Ann. Rev. Neurosc.*, 11:13 (1988), and P. W. Nantyh et al., *Proc. Natl. Acad. Sci.*, 86:5193 (1989), with unlabelled tachykinins displacing their radiolabelled analogues at nanomolar concentrations. In contrast, there was no displacement of any of the tachykinin radioligands by β-amyloid peptide$^{1-40}$ at concentrations up to 30 μM, which indicates that the amyloid peptide does not interact with tachykinin receptors under the standard conditions labelling tachykinin receptors as described. These results were consistent with the reported structure-activity studies among the tachykinin peptide family, namely, that a carboxyl-terminal amide is required for activity.

Radiolabelled rat β-amyloid peptide$^{1-40}$ failed to bind to Alzheimer's disease or normal human tissue, or to adult rat brain. In addition, unlabelled rat β-amyloid peptide$^{1-40}$ did not inhibit deposition of $^{125}$I-β-amyloid peptide$^{1-40}$ onto Alzheimer's disease plaques. These results are consistent with the observation that rodents do not develop amyloid plaques, and indicates that the sequence of the amyloid peptide itself is important in plaque genesis and growth.

The avidity of β-amyloid peptide for amyloid plaques indicates that once an aggregate of amyloid peptide has formed, even extremely low concentrations of β-amyloid peptide will support its growth. It was found that neuritic, diffuse, and vascular plaques were indistinguishable in this capacity. Since neuritic plaques in the cerebral cortex were often surrounded by dying neurons while diffuse plaques in the cerebellum were not, these results indicate that if β-amyloid peptide is neurotoxic, it is selectively neurotoxic to a subset of central neurons.

The use of radioiodinated β-amyloid peptide provides an in vitro system for the quantitative evaluation of agents or conditions which may inhibit or enhance the growth of plaques, a sensitive method for visualizing various types of amyloid deposits, a means for characterizing and locating sites of amyloid peptide binding to cells and tissues, and for investigation of the role of amyloid deposits in the pathogenesis of Alzheimer's disease.

EXAMPLE 3

In Vitro Evaluation of Agents for Inhibiting or Enhancing Aggregation of β-Amyloid Peptide, or for Dispersing Aggregates of β-Amyloid Peptide, in the Absence of Alzheimer's Disease Plaques The experiments described in Example 1 demonstrated that amyloid plaques can grow in vitro by deposition of labeled amyloid peptide from dilute solution. The following experiment with radiolabelled β-amyloid peptide demonstrated that the peptide can aggregate in vitro in the absence of amyloid plaques. This latter property provides an in vitro system for qualitative and quantitative evaluation of agents or conditions that may inhibit or enhance this aggregation or disperse preformed aggregates. Agents so identified may have similar effects on Alzheimer's disease plaques in vivo.

Figure 4:
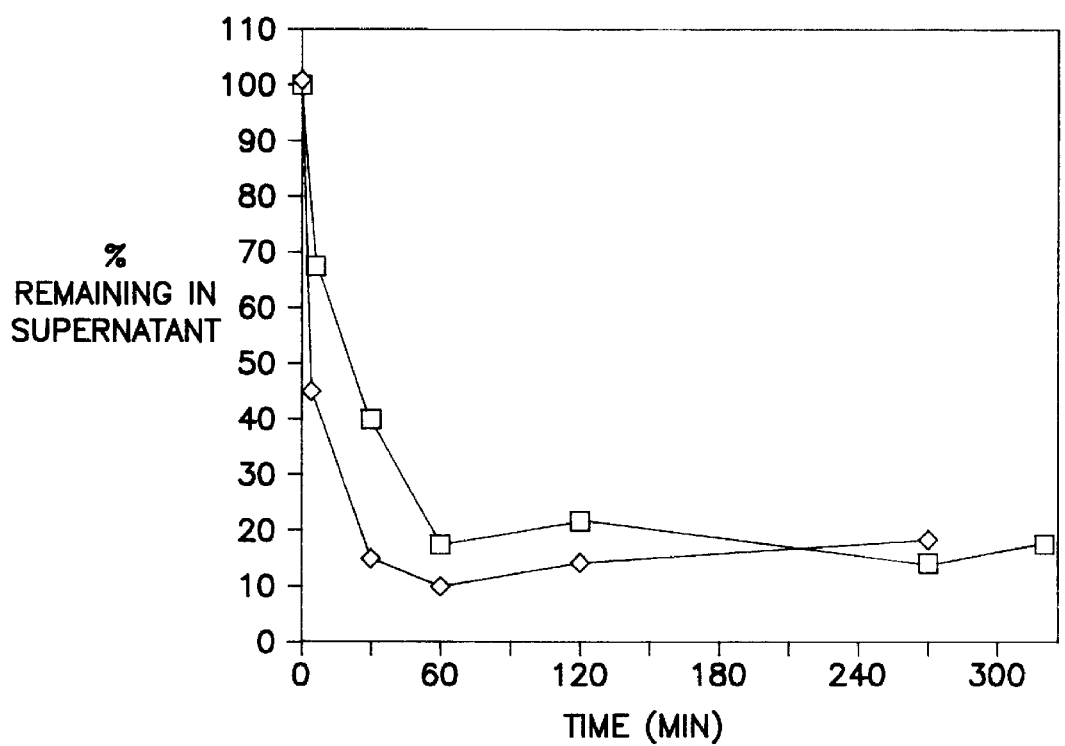
FIG. 4 is graphic depiction of in vitro aggregation of ● human $^{125}$I-β-amyloid peptide$^{1-40}$, and □ human $^{125}$I-β-amyloid peptide$^{1-40}$ in the presence of sodium dodecylsulfate (SDS).

A solution of about $10^{-9}$M labelled β-amyloid peptide in 50 mM Tricine buffer at pH 7.5 was prepared from stock solution of the peptide as described hereinabove in Example 1. The solution was aliquotted into several reaction vessels (polypropylene microcentrifuge tubes) and allowed to stand at room temperature with occasional vortex mixing. At various times, the tubes were centrifuged at 12000g for 4 minutes, and the fraction of initial (t=0) cpm of labelled peptide remaining in the supernatant fraction determined by removing a small aliquot for counting. The time course of the disappearance of the tracer from the supernatant under these conditions is shown in FIG. 4. The rate of disappearance was dependent on a variety of other conditions which were evaluated using this assay. Thus, the rate of the disappearance depends on peptide concentration (faster at higher peptide concentrations), and on ionic strength (faster at higher salt concentrations). The rate of disappearance was further dependent on the presence of certain detergents such as sodium dodecylsulfate (SDS) (faster in 0.01% SDS; see, FIG. 4), and on the presence of certain organic solvents (slower in the presence of acetonitrile).

Methods similar to those described hereinabove may be used to assay the rate of formation of aggregates which may be separated by filtration or centrifugation, or the rate of dispersion of aggregates of amyloid peptide, or the effects of various agents on these processes. In each case, a key step is the use of labelled amyloid peptide in the aggregate or in solution to follow the time course of the process.

EXAMPLE 4

In Vitro Evaluation of Agents for Inhibiting or Enhancing Plaque Growth

The competitive binding assay, as described in FIG. 1, was conducted to determine inhibition of $^{125}$I-β-amyloid peptide$^{1-40}$ aggregation by amyloid and tachykinin peptides in homogenates of Alzheimer's disease temporal cortex. The aggregation affecting agents that were tested included β-amyloid peptide$^{1-40}$, β-amyloid peptide$^{25-35}$-NH$_2$, β-amyloid peptide$^{25-35}$-OH, rat β-amyloid peptide$^{1-40}$, substance P, and neurokinins A and B.

As shown in Table II, patients considered to have Alzheimer's disease were clinically diagnosed as such, and contained numerous plaques, as determined by thioflavin S staining of brain tissue samples. Control subjects were age-matched patients with no history of dementia.

Tissue homogenates of temporal cortex tissue obtained from the control subjects were prepared according to the protocol set forth in Example 1. Autoradiography, also as set forth in Example 1, indicated the absence of amyloid plaques in the homogenized tissue material. (See, Table II). As the tissue samples displayed no evidence of Alzheimer's disease, the samples were considered "normal" tissue, and used as controls.

Tissue homogenates of temporal cortex tissue obtained from patients with Alzheimer's disease were also prepared according to Example 1 (See, Table II). Autoradiography detected amyloid plaques in the homogenized tissue material.

Inhibition of $^{125}$I-β-amyloid peptide$^{1-40}$ deposition was determined by adding increasing concentrations of the deposition affecting agents/peptides to the incubation medium and determining the percent inhibition of deposition. FIG. 1 shows that whereas β-amyloid peptide$^{1-40}$ or Dutch β-amyloid peptide$^{1-40}$ are potent inhibitors of $^{125}$I-β-amyloid peptide$^{1-40}$ deposition, β-amyloid peptide$^{25-35}$-NH$_2$ is substantially less potent and substance P, Neurokinin A and B, β-amyloid peptide$^{25-35}$ —OH, and rat β-amyloid peptide$^{1-40}$ are essentially inactive. This shows the usefulness of this assay in assessing an agent's ability to inhibit β-amyloid peptide$^{1-40}$ deposition to pre-formed plaques.

EXAMPLE 5

Localization of $^{125}$I-β-Amyloid Peptide$^{1-40}$ Binding Sites in Alzheimer's Disease Brain Tissue Tissue sections of Alzheimer's disease temporal cortex from Example 3 were examined by autoradiography to detect binding sites of $^{125}$I-β-amyloid peptide$^{1-40}$.

There was no specific deposition of β-amyloid peptide$^{1-40}$ in the absence of plaques. As shown in FIG. 2, an autoradiograph of $^{125}$I-β-amyloid peptide$^{1-40}$ binding in tissue sections of Alzheimer's disease temporal cortex, tissue from areas without plaques showed no binding of $^{125}$I-β-amyloid peptide$^{1-40}$ which could be displaced by excess β-amyloid peptide$^{1-40}$.

Figure 2A:
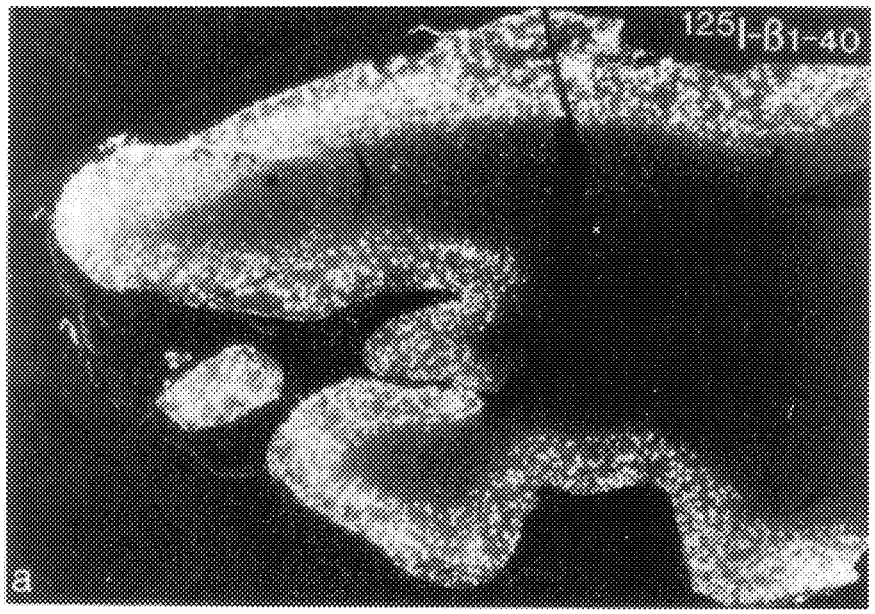
FIGS. 2a–2h are an autoradiographic localization of $^{125}$I-β-amyloid peptide$^{1-40}$ binding sites in Alzheimer's disease brain.
Figure 2B:
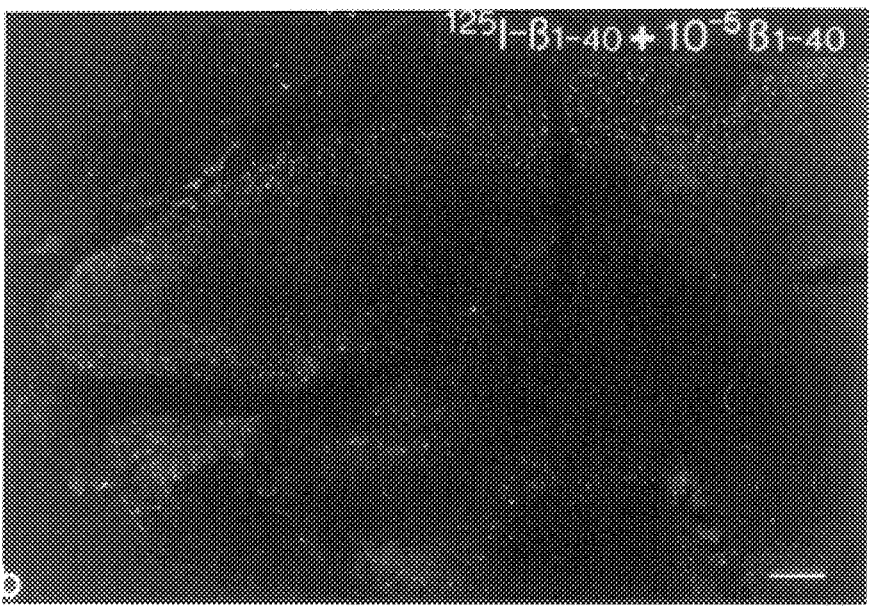
Figure 2C:
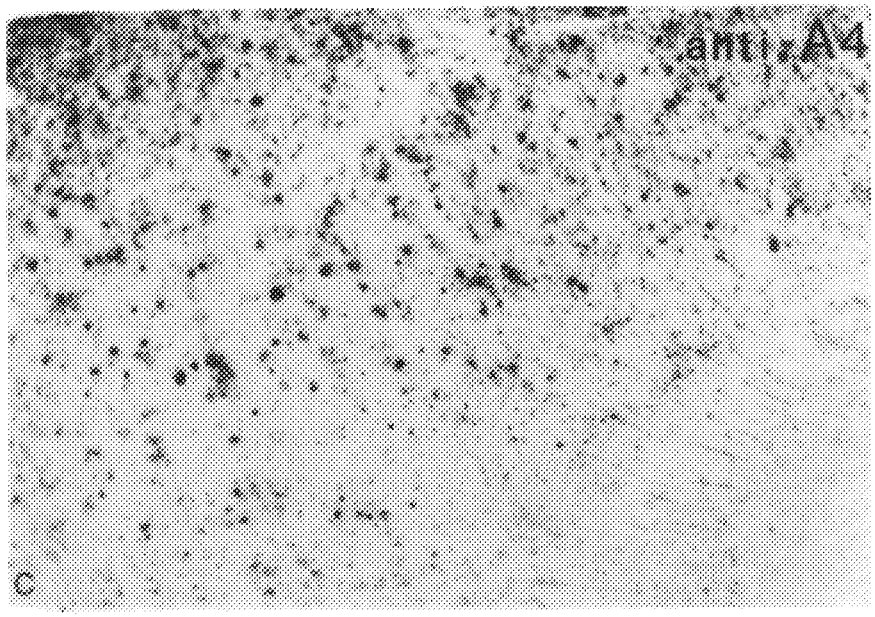
Figure 2D:
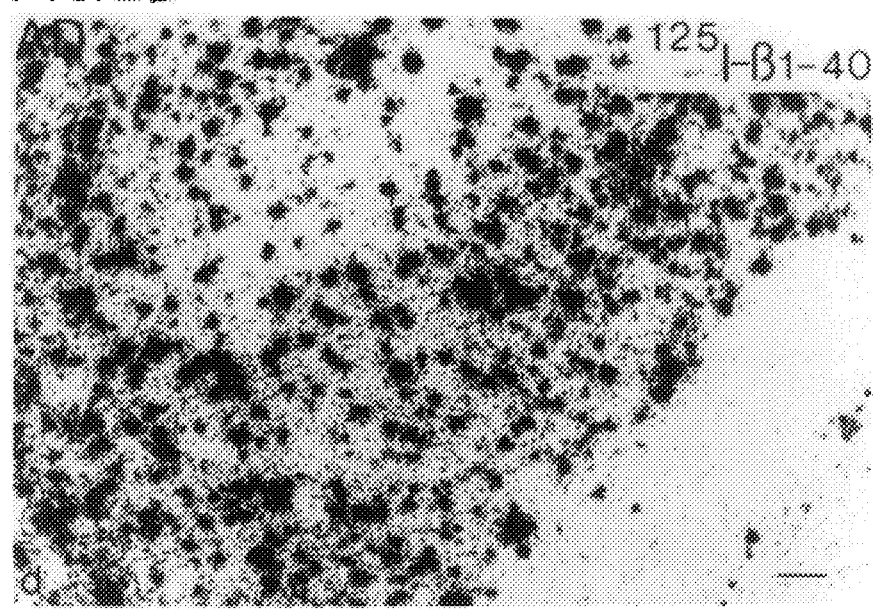
Figure 2E:
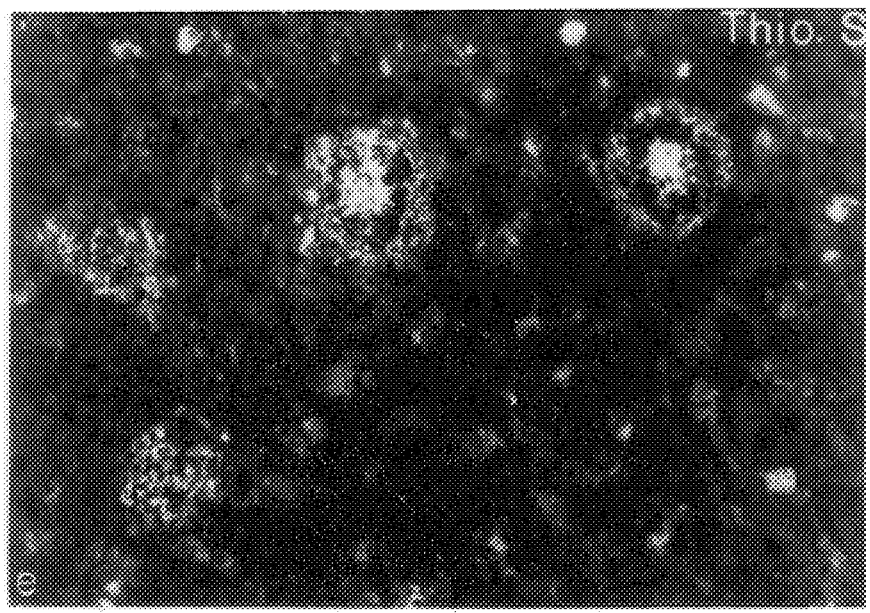
Figure 2F:
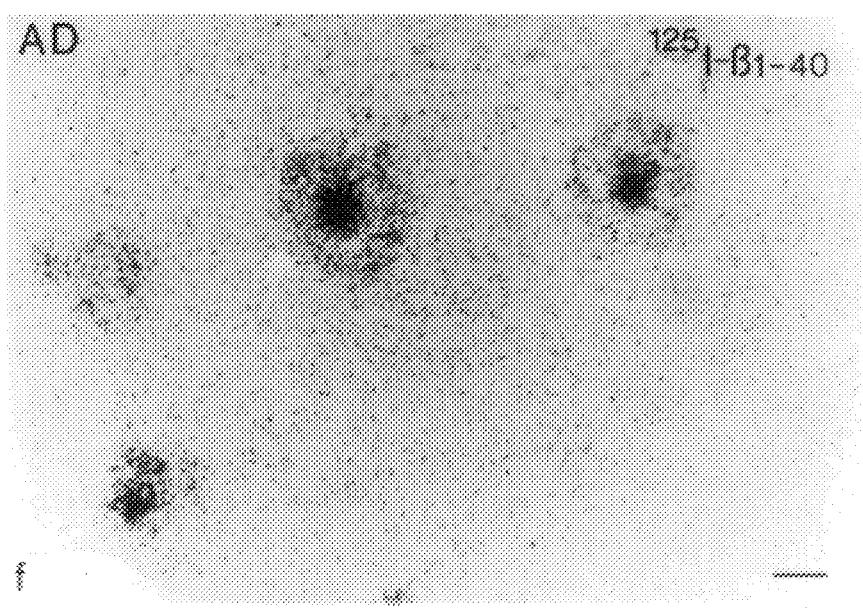
Figure 2G:
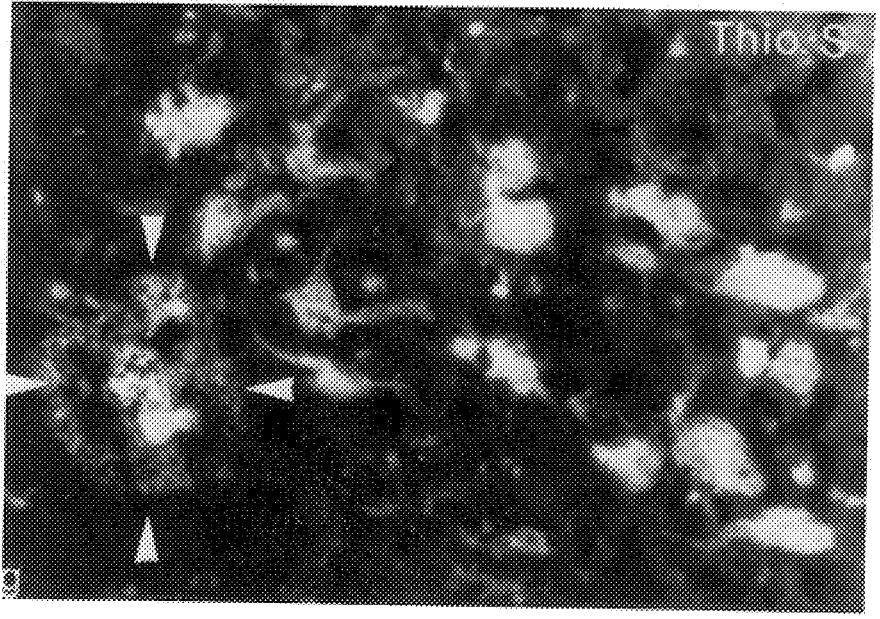
Figure 2H:
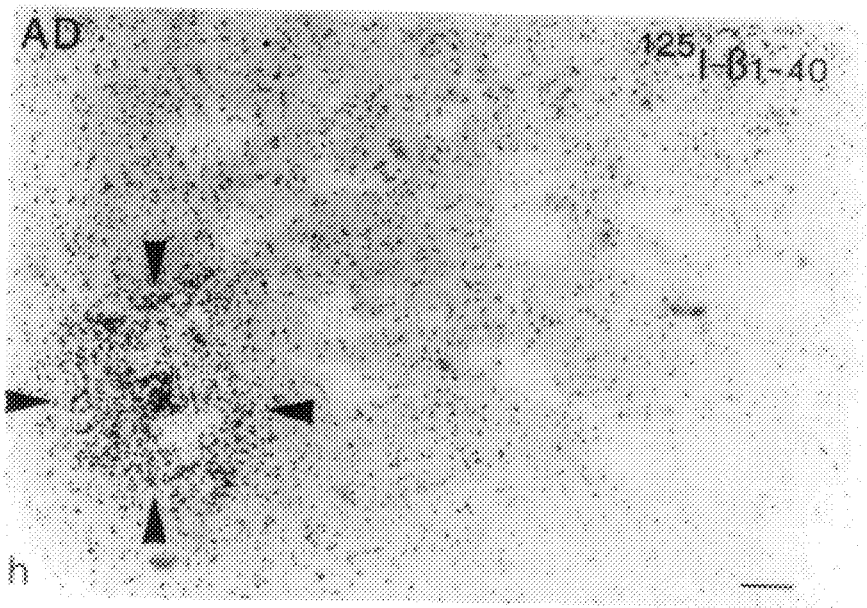

A dark field photomicrograph showing the distribution of $^{125}$I-β-amyloid peptide$^{1-40}$ in Alzheimer's disease temporal cortex revealed numerous plaques throughout the grey matter (FIG. 2(a)). A dark-field micrograph of a serially adjacent section as treated in FIG. 2(a), except that $10^{-5}$M cold β$_{1-40}$ was added to the incubation medium, is shown in FIG. 2(b). An immunohistochemistry of amyloid deposits using antibodies raised against β-amyloid peptide$^{1-40}$ (amyloid peptide A4) in Alzheimer's disease temporal cortex is shown in FIG. 2(c). FIG. 2(d) is a dark-field photomicrograph of the same section as shown in FIG. 2(c), where $^{125}$I-β-amyloid peptide$^{1-40}$ revealed a more extensive distribution of plaques than did the anti-A4 antibody. FIG. 2(e) is a dark-field photomicrograph of thioflavin S staining in human Alzheimer's disease temporal cortex showing labelling of diffuse, compact and neuritic type plaques. FIG. 2(f) is a light-field photomicrograph of the same section as FIG. 2(e) bound with $^{125}$I-β-amyloid peptide$^{1-40}$, showing that all three types of plaques bind $^{125}$I-β-amyloid peptide$^{1-40}$. FIG. 2(g) is a dark-field photomicrograph of thioflavin S staining in human Alzheimer's disease temporal cortex showing labelling of a neuritic plaque and several adjacent neurons. FIG. 2(f) is a light-field photomicrograph showing the same section as FIG. 2(g), bound with $^{125}$I-β-amyloid peptide$^{1-40}$, showing that although both the core and halo of the plaque bind $^{125}$I-β-amyloid peptide$^{1-40}$, none of the labeled neurons show any $^{125}$I-β-amyloid peptide binding.

Localization of $^{125}$I-β-amyloid peptide$^{1-40}$ binding sites in the cerebral vasculature of Alzheimer's disease brain is shown in FIG. 3. FIG. 3(a) shows the distribution of $^{125}$I-β-amyloid peptide$^{1-40}$ in plaques in the parenchyma and in blood vessels (BV) in Alzheimer's disease temporal cortex. FIG. 3(b) shows a serially adjacent section treated in the as that of FIG. 3(a), except that 5.0×10$^{-5}$M cold β-amyloid peptide$^{1-40}$ was added in the incubation medium.

Figure 3A:
FIGS. 3a–3d are an autoradiographic localization of $^{125}$I-β-amyloid peptide$^{1-40}$ binding sites in the cerebral vasculature of Alzheimer's disease brain tissue.
Figure 3B:
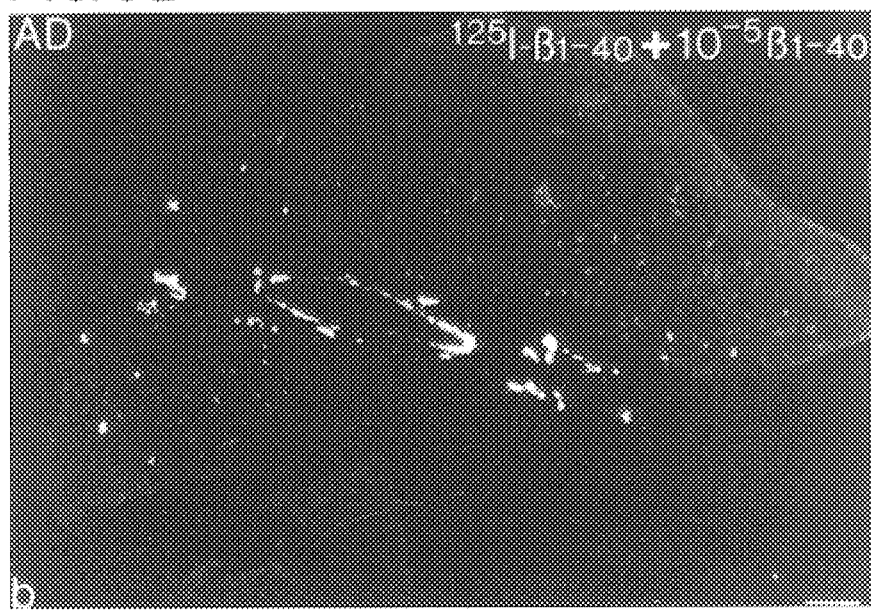
Figure 3C:
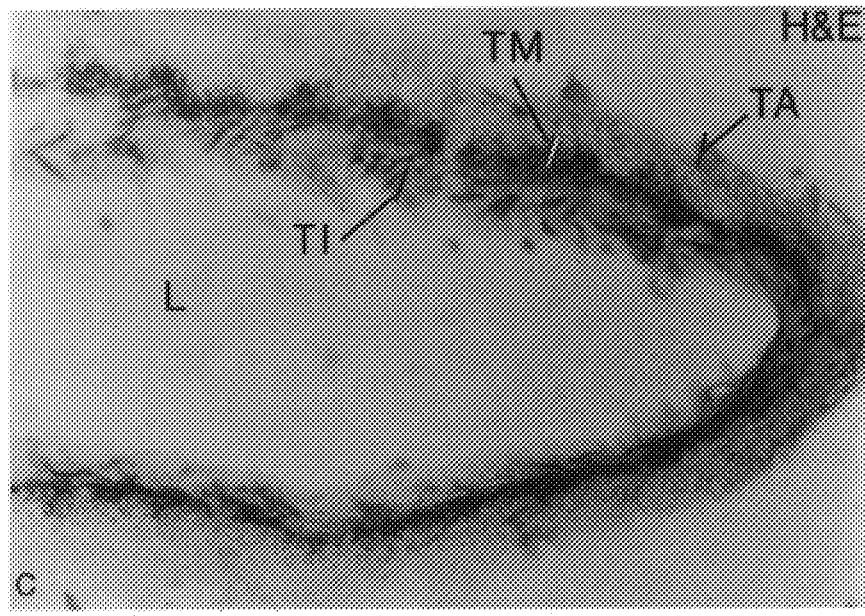
Figure 3D:
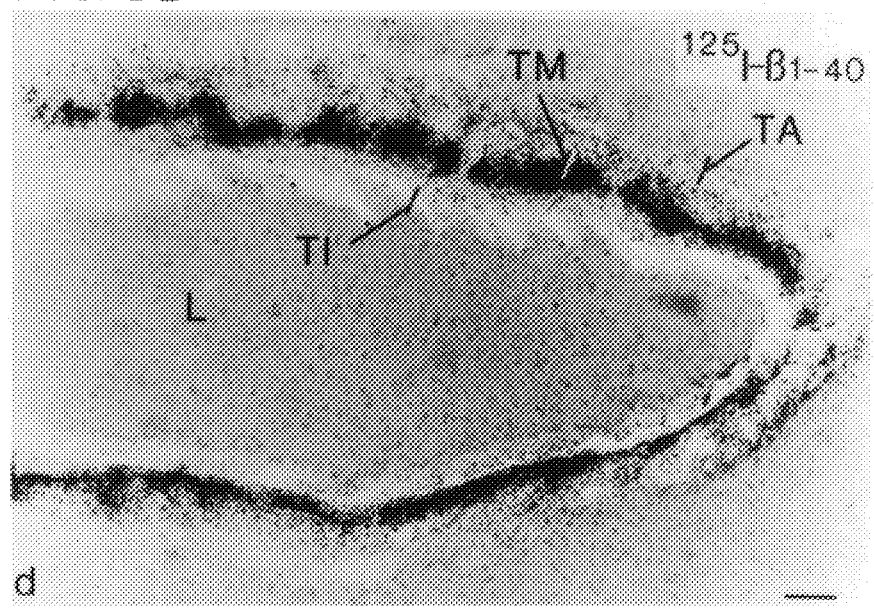

FIG. 3(c) is a light-field photomicrograph showing the localization of $^{125}$I-β-amyloid peptide$^{1-40}$ in a cerebral artery. FIG. 3(d) is a dark-field photomicrograph of the same section as in FIG. 3(c) showing the binding of $^{125}$I-β-amyloid peptide over the tunica media of the cerebral artery.

The invention has been described with reference to various specific and preferred embodiments and techniques. However, it should be understood that many variations and modifications may be made while remaining within the spirit and scope of the invention.

What is claimed is:

1. An in vitro method of screening for an agent capable of affecting the deposition of β-amyloid peptide or peptide fragment thereof on tissue, the method comprising:
   (a) combining a sample of human tissue evidencing the presence of Alzheimer's amyloidosis, with an amount of labelled β-amyloid peptide or labelled active peptide fragment thereof and an agent to be screened for a time effective to allow binding of the labelled β-amyloid peptide of the labelled fragment thereof to amyloid plaques in the tissue;
   (b) detecting the amount of labelled β-amyloid peptide or labelled peptide fragment bound to the tissue sample; and
   (c) assessing the effect the agent has on β-amyloid peptide or peptide fragment deposition.

2. The method according to claim 1, wherein the label of the labelled β-amyloid peptide or labelled active peptide fragment thereof comprises a radiolabel, an enzyme label, a fluorescent label, a chemiluminescent label, or an antigen label.

3. The method of claim 2, wherein the presence of the labelled β-amyloid or labelled active peptide fragment thereof bound to amyloid plaques in the tissue sample is detected by autoradiography, positron emission tomography, nuclear magnetic resonance imaging, a gamma counter, or a scintillation counter.

4. The method according to claim 1 wherein the labelled peptide or labelled active peptide fragment is radiolabelled.

5. The method according to claim 4, wherein the peptide or labelled active peptide fragment is radiolabelled with radioactive iodine.

6. The method according to claim 1, wherein the β-amyloid peptide that is labelled has the amino acid sequence as set forth in SEQ. ID NO:1 prior to labelling.

7. The method according to claim 1, wherein the β-amyloid peptide that is labelled has the amino acid sequence as set forth in SEQ. ID NO:2 prior to labelling.

* * * * *

UNITED STATES PATENT AND TRADEMARK OFFICE
CERTIFICATE OF CORRECTION

PATENT NO.: 5,837,473
DATED: November 17, 1998
INVENTOR(S): John Edward Maggio et al.

It is certified that error appears in the above-identified patent and that said Letters Patent is hereby corrected as shown below:

Title page, 1 Column, under "Other Publications", D.Allsop et al. entry, delete "Immunohistomchemical" and insert --Immunohistochemical--;

Title page, 2nd Column, J.F. Flood et al. entry, 3rd line, delete "Alheizmers" and insert --Alzheimer--;

Title page, 2nd Column, J. Kang et al. entry, 2nd line, delete "protien" and insert --protein--;

Title page, 2nd Column, D.A. Kirshner et al. entry, 2nd line, delete "protien" and insert --protein--;

Title page, 2nd Column, J.E. Maggio entry, delete "Tachykinis" and insert --Tachykinins--;

Page 2, 2nd Column, delete "J.S. Whitsin et al." and insert --J.S. Whitson et al.--;

Page 2, 2nd Column, B.A.Yanker et al. entry, 2nd line, delete "Effects of";

Column 2, line 15, delete "H-DAEFRHDSGYEVHHQKLVFFAEDVGSNKGAIIGL'-" and insert --H-DAEFRHDSGYEVHHQKLVFFAEDVGSNKGAIIGL--;

Column 6, lines 29-30, delete "peptide 40 technique" and insert --peptide$^{1-40}$ technique--;

Column 6, Table II, line H 023-R, column p$^{4,6}$, insert --++++--;

UNITED STATES PATENT AND TRADEMARK OFFICE
CERTIFICATE OF CORRECTION

PATENT NO.: 5,837,473
DATED: November 17, 1998
INVENTOR(S): John Edward Maggio et al.

It is certified that error appears in the above-identified patent and that said Letters Patent is hereby corrected as shown below:

Column 8, line 58, delete "A-amyloid" and insert --β-amyloid--;

Column 10, lines 15-16, delete "peptide $^{25}$-$_{35}$-NH$_2$" and insert --peptide $^{25-35}$-NH$_2$--;

Column 12, line 13, delete "In Vivo" and insert --In Vitro--;

Column 14, line 24, delete "peptide 1-40" and insert --peptide$^{1-40}$--; and

Signed and Sealed this

Fifth Day of December, 2000

Attest:

Attesting Officer

Q. TODD DICKINSON

Director of Patents and Trademarks